(12) United States Patent
Savelkoul et al.

(10) Patent No.: US 9,506,109 B2
(45) Date of Patent: Nov. 29, 2016

(54) MICROBIAL POPULATION ANALYSIS

(75) Inventors: Paul Hendrik Maria Savelkoul, Amsterdam (NL); Andries Edward Budding, Amsterdam (NL)

(73) Assignee: Microbiome Limited, Houten (NL)

( * ) Notice: Subject to any disclaimer, the term of this patent is extended or adjusted under 35 U.S.C. 154(b) by 49 days.

(21) Appl. No.: 12/596,166

(22) PCT Filed: Apr. 17, 2008

(86) PCT No.: PCT/EP2008/003200
§ 371 (c)(1),
(2), (4) Date: Feb. 2, 2010

(87) PCT Pub. No.: WO2008/125365
PCT Pub. Date: Oct. 23, 2008

(65) Prior Publication Data
US 2010/0129816 A1    May 27, 2010

(30) Foreign Application Priority Data
Apr. 17, 2007 (EP) ..................................... 07075289

(51) Int. Cl.
*C12Q 1/68* (2006.01)
*C07H 21/02* (2006.01)

(52) U.S. Cl.
CPC .................................. *C12Q 1/6844* (2013.01)

(58) Field of Classification Search
CPC ............ C12Q 1/6844; C12Q 2525/15; C12Q 2537/143
See application file for complete search history.

(56) References Cited

U.S. PATENT DOCUMENTS

| | | | |
|---|---|---|---|
| 7,202,027 B1 * | 4/2007 | Grabowski et al. ......... | 435/6.16 |
| 7,803,534 B2 | 9/2010 | Ito et al. | |
| 2004/0176584 A1 | 9/2004 | Terlesky | |
| 2005/0176001 A1 * | 8/2005 | Nakano et al. ................... | 435/6 |
| 2007/0054300 A1 | 3/2007 | Parada Valdecantos et al. | |

FOREIGN PATENT DOCUMENTS

| | | | |
|---|---|---|---|
| EP | 1 696 039 | | 8/2006 |
| WO | WO-93/04201 | | 3/1993 |
| WO | WO-01/23604 | | 4/2001 |
| WO | WO 01/23606 | * | 4/2001 |
| WO | WO-2004/052175 | | 6/2004 |
| WO | WO-2005/080600 | | 1/2005 |

OTHER PUBLICATIONS

Fierer, N. et al., Appl. Env. Microbiol., vol. 71, pp. 4117-4120 (2005).*
Dethlefsen, L. et al., TRENDs in Ecology and Evolution, vol. 21, pp. 517-523 (Jul. 2006).*
Eckburg, P.B. et al., Science, vol. 308, pp. 1635-1638 (2005).*
Nakanishi, Y. et al., Appl. Env. Microbiol., vol. 72, pp. 6271-6276 (Sep. 2006).*
Kricka, L., Ann. Clin. Bioch., vol. 39, pp. 114-129 (2002).*
Mata, A.I. et al., Appl. Env. Microbiol., vol. 70, pp. 3183-3187 (2004).*
Mahony, J.B. et al., J. Clin. Microbiol., vol. 33, pp. 3049-3053 (1995).*
Hendolin, P.H. et al., J. Clin. Microbiol., vol. 35, pp. 2854-2858 (1997).*
Grondahl, B. et al., J. Clin. Microbiol., vol. 37, pp. 1-7 (1999).*
Klausegger, A. et al., J. Clin. Microbiol., vol. 37, pp. 464-466 (1999).*
Blackwood, C.B. et al., Appl. Env. Microbiol., vol. 71, pp. 6193-6198 (2005).*
Turenne, C.Y., Thesis, Master of Science, University of Manitoba, pp. 1-138 (1998).*
SigmaAldrich, Fluorescent probes, pp. 1-12; downloaded from www.sigmaaldrich.com/etc/medialib/docs/Sigma/Brochure/fluorescent_dna_probes.Par.0001.File.tmp/fluorescent_dna_probes.pdf Oct. 28, 2013.*
Uphoff, H.U. et al., FEMS Microbiology Ecol., vol. 35, pp. 249-258 (2001).*
Watanabe, K. et al., J. Microbiol. Meth., vol. 44, pp. 253-262 (2001).*
Baker, G.C. et al., J. Microbiol. Meth., vol. 55, pp. 541-555 (2003).*
International Search Report dated Aug. 6, 2008 from PCT/EP2008/003200.
Singh et al., "Use of Multiplex Terminal Restriction Fragment Length Polymorphism for Rapid and Simultaneous Analysis of Different Components of the Soil Microbial Community," Applied and Environmental Microbiology, 72(11):7278-7285 (2006).
Liu et al., "Rapid identification of the species of the *Bacteroides fragilis* group by multiplex PCR assays using group- and species-specific primers," FEMS Microbiology Letters, 222(1):9-16 (2003).
Anonymous: "IBIS—Integrated Biotechnological Information Services, Job Result Dossier SA803571," Dec. 11, 2014, XP055158292, Retrieved from the Internet: URL:http://ibis.internal.epo.org/exam/jobResult?id=297438 [retrieved on Dec. 12, 2014].

* cited by examiner

*Primary Examiner* — Teresa Strzelecka
(74) *Attorney, Agent, or Firm* — Foley Hoag LLP (57) ABSTRACT

The current invention relates to a method for analysis of a population of micro-organisms (e.g. bacterial population) of different taxonomic groups in an environment suspected to contain said bacteria, primers, primer sets and pair of primer sets suitable for use is such method, and use of such method in determining the effect of external factors like drugs, nutrients and pesticides on bacterial populations of different taxonomic groups.

20 Claims, 4 Drawing Sheets

SEQUENCE LISTING

<160> NUMBER OF SEQ ID NOS: 13

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
ctggatcacc tcctttctaw g                                            21

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
ctggaacacc tcctttctgg a                                            21

<210> SEQ ID NO 3
<211> LENGTH: 20
<212> TYPE: DNA
<213> ORGANISM: Artificial

```
<220> FEATURE:
<223> OTHER INFORMATION: primer

<400> SEQUENCE: 3
aggcatccac cgtgcgccct                                               20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
aggcattcac crtgcgccct                                               20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
aggcatccrc catgcgccct                                               20

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
ggcatccacc gtgtacgct                                                19

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
ttggatcacc tccttacctw a                                             21

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
acgttaactt cggccgggaa aggggggttt                                    30

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
tacacggtga gccatcatca tgggttt                                       27
```

```
<210> SEQ ID NO 10
<211> LENGTH: 27
<212> TYPE: DNA
<213> ORGANISM: Artificial
<220> FEATURE:
<223> OTHER INFORMATION: primer

<400> SEQUENCE: 10
acgtcatcac tgttcccccc cgggttt                                              27

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
acgttaactt cggccgggaa aggggggttt                                           30

<210> SEQ ID NO 12
<211> LENGTH: 27
<212> TYPE: DNA
<213> ORGANISM: Artificial
<220> FEATURE:
<223> OTHER INFORMATION: primer

<400> SEQUENCE: 12
tacacggtga gccatcatca tgggttt                                              27

<210> SEQ ID NO 13
<211> LENGTH: 27
<212> TYPE: DNA
<213> ORGANISM: Artificial
<220> FEATURE:
<223> OTHER INFORMATION: primer

<400> SEQUENCE: 13
acgtcatcac tgttcccccc cgggttt                                              27
```

MICROBIAL POPULATION ANALYSIS

RELATED APPLICATIONS

This application is the U.S. National Stage Application of International Application No. PCT/EP2008/003200, filed on Apr. 17, 2008, which claims the benefit of priority to the European Patent Application No. 07075289.4, filed on Apr. 17, 2007; the contents of each of which application is incorporated herein in its entirety by this reference.

The current invention relates to a method for analysis of populations of micro-organisms like bacterial populations of different taxonomic groups in an environment suspected to contain said micro-organisms, primers, primer sets and pair of primer sets suitable for use is such method, and use of such method in determining the effect of external factors like drugs, nutrients and pesticides on such populations.

In a recent article (Science (2005) Volume 308(5728): 1635-8) Eckburg and colleagues described the enormous diversity of the human intestinal microbial flora. They reported the presence of at least 395 bacterial phylotypes of which at least 244 were novel and 80% represented sequences from species that have not been cultivated.

Most of the inferred organisms were members of the Firmicutes and Bacteroidetes phyla, and most of the Firmicutes sequences were members of the Clostridia class. Other phyla detected were Proteobacteria, Actinobacteria, Fusobacteria and Verrucomicrobia.

It is generally accepted that a better understanding of the composition of the intestinal microflora will be of decisive importance in understanding the fundamental role of the microflora in health and disease (for example in Crohn's disease, immunity, metabolic disease, allergy, disturbances in the probiotic activity, protection against cell injury, regulation of host fat storage, stimulation of intestinal angiogenesis and the like), yet these types of ecosystems remain incompletely characterized and its diversity is very poorly defined.

A major draw-back is that in order to obtain such data as described by Eckburg, extremely laborious and time-consuming experiments have to be performed. Although the provided information is invaluable for the scientific community, it is nevertheless too laborious and time-consuming to perform such analysis on a regular and routine basis, for example in medical practice. Moreover variations associated with time, diet and health status in the composition of micro-organisms have not been adequately studied.

Understanding of such bacterial populations is limited and hindered by the absence of reliable, reproducible and less time consuming or less laborious methods that would allow for analysis of these populations of micro-organisms.

Another example of an environment wherein it is believed that the composition of the microbial communities is of high importance is water. For example, Ibekwe describes (in J. Appl. Microbiol. 102(4):921-936 (2007)) that wetlands with 50% plant cover may promote the growth of diverse microbial communities that facilitate decomposition of chemical pollutants in surface water, and improve water quality. Better understanding of such systems and how these systems are influenced by external factors will help in improving water quality.

Yet another example is bacterial ecosystems in food stuffs. For example, El-Baradei (in Appl Environ Microbiol. 2007 February; 73(4):1248-55) describes the biodiversity of bacterial ecosystems in traditional Egyptian Domiati cheese. The biodiversity in the cheese was studied by PCR-temporal temperature gel electrophoresis (TTGE) and PCR-denaturing gradient gel electrophoresis (DGGE). Dominant lactic acid bacteria were identified, whereas also non-lactic acid bacteria were found. El-Baradei suggests that these bacteria have an important role in the ripening process. In other words, a better understanding of the population of micro-organisms involved in the ripening of cheese is useful for further product improvement.

However, understanding of the population of micro-organisms and use and study thereof is currently limited due to the absence of reliable, reproducible and less time consuming methods that allow for suitable analysis of such complex microflora of unknown composition.

Several methods suitable for identification of known bacteria are described in the art.

WO 00/52203 describes a method for identifying bacteria which comprises amplifying a portion of the 23S rDNA present in the sample using, as one primer, a degenerate primer set comprising one or more DNA molecules consisting essentially of DNA having the sequence 5'GCGATTTCYGAAYGGGGRAACCC, the other primer consisting of DNA having the sequence 5'TTCGCCTTTC-CCTCACGGTACT and testing the resulting amplicon by hybridization to one or more oligonucleotide probes designed to identify one or more bacteria. The method is limited to the identification of known bacteria and requires the use of probes specifically directed to such bacteria.

WO 02/090582 relates to a method for detection of mycobacteria, based on the 23S/5S spatial region of mycobacteria. It is described that for the analysis of said mycobacteria a first primer can be chosen that is specific for the genus, whereas a second primer that is species-specific might be chosen.

WO 01/23606 relates to nucleic acid molecules which allow the identification of bacteria or groups of bacteria. The region containing 23S/5S rDNA and pertaining to the bacterial genome is used as the target sequence for detecting the bacteria. According to the inventors the 16S/23s rDNA is under scrutiny with respect to a region for use in the identification of bacteria. The groups of bacteria are identified by performing a consensus PCR, followed by amplification of the obtained DNA by the use of more specific primers for subsequent identification of the bacteria at different taxonomic levels. Such consensus PCR can be performed by providing primers for different groups within the same taxonomic level (e.g. genus, thereby amplifying two different genuses in one PCR). A drawback is that subsequent reactions have to be performed, introducing uncertainty with respect to meticulousness or accuracy of the analysis, whereas no data can be provided with respect to for example the relative amounts of particular micro-organisms in such population.

In other words, the methods described above might be useful when one already knows were one is looking for, but of less use when the population to be studies is of high complexity as a consequence of the presence of many and/or unknown bacteria. In addition, the idea that not the individual micro-organisms, but the complex interactions and relative amounts of micro-organisms in a population are important is gaining in popularity. However, the methods described only have limited use in such understanding. Therefore there is a clear need for non-laborious, reliable methods for analyzing (the composition of) a population of micro-organisms. Such methods should be applicable on a routine basis and provide at least information with respect to the overall composition of the population.

It has now surprisingly been found by the current inventors that at least one of the above mentioned problems can be solved by the subject matter as described in the accompanying claims.

More in particular it has been found that a method for analysis of populations of micro-organisms, like bacterial populations of different taxonomic groups, in an environment suspected to contain said micro-organisms solves at least one of the above mentioned problems, the method comprising the steps of a. providing DNA obtained from said environment and providing thereto at least
   i. a first primer set P1, comprising at least one primer p1, that is directed to at least one conserved location L1 specific for a first taxonomic group selected from the group consisting of phylum, class, order or family;
   ii. a second primer set P2, comprising at least one primer p2, that is directed to at least one conserved location L2 specific for a second taxonomic group selected from the group consisting of phylum, class, order or family;
   iii. a third primer set P3, comprising of at least one primer p3, that is directed to at least one conserved location L3 that is at least specific for micro-organisms belonging to the first taxonomic group;
   iv. a fourth primer set P4, comprising of at least one primer p4, that is directed to at least one conserved location L4 that is at least specific for microorganisms belonging to the second taxonomic group, and wherein the primer sets P1 and P3 are suitable for amplifying a region between said conserved regions L1 and L3 and wherein the primer sets P2 and P4 are suitable for amplifying the region between said conserved regions L2 and L4;
b. performing an amplification reaction using said primer sets, thereby producing fragments having detectable differences in size, number, nucleotide sequence and/or label; and
c. detecting said differences.

It has surprisingly been found that with the method it is now possible to detect in a reliable, non-laborious manner the overall composition of a population of micro-organisms, for example a bacterial population.

As will be clear to the person skilled in the art, the primers and primer sets used in the method according to the invention are, in contrast with the methods available in the art, not directed to identification of individual microorganisms (bacteria) in a population, but are as such that the overall population is analyzed, both with respect to specific taxonomic groups and with respect to other differences like differences in length, size and sequence of the obtained fragments.

As will be understood by the skilled person the term "at least one primer" does not refer to the number of copies of the primer present, but to the type of primers used (as defined by its sequence).

Such analyses now for the first time makes it possible to obtain in an easy and straight forward manner a "fingerprint" of the population of micro-organisms, for example a bacterial population. Such fingerprint comprises at least information with respect to the different taxonomic groups present in a population of micro-organisms, and for example the overall composition (as expressed by differences in length, sequence and the like of the obtained fragments) of such taxonomic group mentioned in the method described above.

As is clear from above, the experiment can advantageously be performed using primers sets according to the invention simultaneously present in one sample. In other words, advantageously, to a sample comprising DNA, according to the invention, the at least primer sets P1, P2, P3 and P4 (or at least primers p1, p2, p3 and p4 according to the invention) are present in (or added to) the same sample. Consequently, and with advantage, PCR is performed under equal conditions for all primers.

With respect to the use of different terms throughout the current disclosure the following definitions apply:

"bacterial population" is the group of bacteria inhabiting a particular environment. Well-known examples are gastrointestinal populations, biofilms, bacterial mats, group of bacteria living in soil or in the rizosphere of plants and aqueous environments, like water.

"population of micro-organisms" is the group of micro-organisms, as used within the context of the current invention, inhabiting a particular environment.

"taxonomic group" is a taxon with all its subordinate taxa and their individuals. Example of taxonomic groups known by the skilled person are (from general to more specific) domain, kingdom, phylum, class, order, and family. Also genus and species are taxa.

"environment" refers to the complex of surrounding circumstances, conditions, or influences in which the population of micro-organisms is situated. Non-limiting examples are the gastrointestinal tract, tooth pockets, soil, rizosphere.

"primer" is a nucleic acid strand (or related molecule) that serves as a starting point for DNA replication. In particular a primer can consists of from 3-50 nucleotides, typically and preferably from 10-30 nucleotides.

"primer set" is a set comprising at least one primer. Within the context of the current invention said primer set can be directed to at least one conserved location.

"conserved location" is a sequence comprising multiple nucleotides and that shares a high homology within the taxonomic group to which the primer is directed. In general this is meant to construe that said sequence is essentially identical in at least 60%, preferably 70%, more preferably 80%, even more preferably 90% of the known micro-organisms belonging to said taxonomic group, and wherein essentially identical means that no more than 8, more preferably no more than 7, 6, 5, 4, 3, 2, or 1 nucleotide is different. In any case, a location is considered conserved within the context of the current invention when it can be suitable used for binding of a primer and allowing to discriminate micro-organisms from one taxonomic group from the other, i.e. a primer is specific for at least one taxonomic group when it will not or essentially not bind to a substantial part of the sequences derived from known micro-organisms of another taxonomic group and that is analyzed with the method according to the invention. For example a primer might detect phylum A and B, but not phylum C. In such case the primer is specific for phylum A and B, and is thus directed to a conserved location in phylum A and B, whereas said conserved location is absent in phylum C.

The terms and consequences of the terms "phylum", "class", "order", or "family" are known to the person skilled in the art.

"directed to" as used in the method above relates to a primer or primer set that will hybridize with at least 60%, preferably at least 70%, more preferably at least 80%, most preferably with at least 90% of the known genomes of micro-organisms of a particular taxonomic group for which the primer is intended (see also above under "conserved location").

"region" as described in the method above refers to a nucleotide sequence between two conserved locations. Typically said sequence can comprise from 10-1500 nucleotides.

"amplification reaction" refers to any procedure that can be suitable used for amplification of the DNA sequence of a region between two conserved locations as described herein. Suitable examples include PCR.

"difference is size" or "difference is length" refers to fragments of different nucleotide length, for example due to amplification of length polymorphisms between different microorganisms like bacteria (see for example Gurtler et al. Microbiology. 1995; 141:1255-65.

"difference is amount" refers to differences in the number of copies of the fragments found in the population of micro-organisms. Said differences are indicative for the relative amount of micro-organisms in a particular population.

"difference in nucleotide sequence" refers to differences in the amplified fragments as observed after for example sequencing of the obtained fragments.

"detecting said differences" can be by any suitable mean known to the person skilled in the art.

The term "micro-organism" as used in the context of the current invention includes bacteria, archaea, protists, fungi and also virus. Within the context of the current invention, when the term bacterial, bacterial population or bacteria is/are used, also populations or species of the above mentioned micro-organisms can be encompassed, unless otherwise indicated.

The sequences of primers and oligonucleotides as given herein are expressed in standard IUB/IUPAC nucleic acid code.

Figure 1:
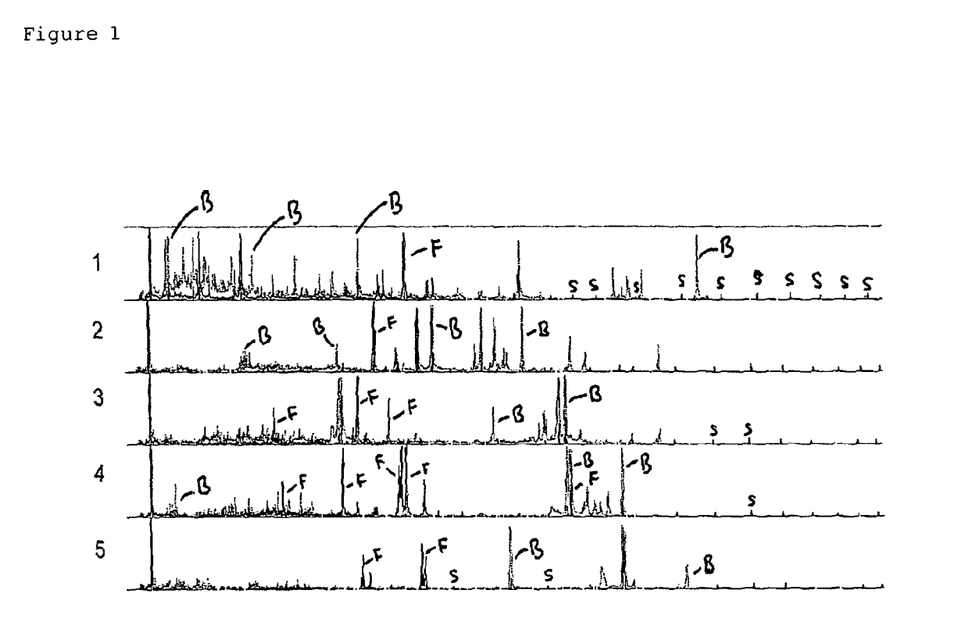
FIG. 1 shows, from left to right, the length of the fragments runs from 0 base pairs to 1000 base pairs obtained from 5 biopsy samples obtained from human intestines as described in Examples 1-4. The small peaks indicated with an "s" are examples of size markers, allowing relating the size of the different obtained fragments. Peaks indicated with a letter "B" represent Hex-labeled fragments of bacteria from the phylum *Bacteroidetes*. Peaks indicated with a letter "F" are examples of FAM-labeled products of bacteria from the phyla *Firmicuta en Actinobacteria*.
Figure 2:
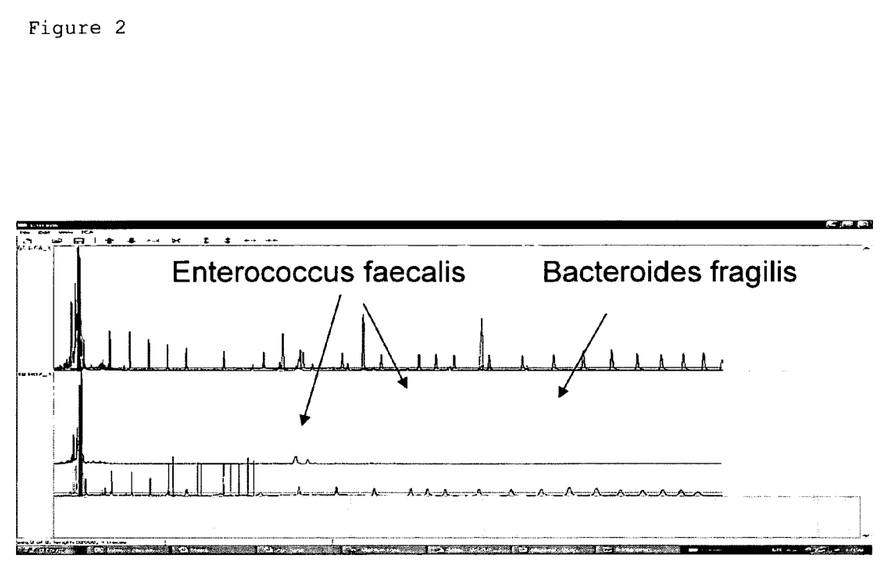
FIG. 2 shows the results of an embodiment of a method as taught herein to a so-called mixed culture of *Enterococcus faecalis* (belonging to the *Firmicuta*) and *Bacteroides fragilis*, belonging to the phylum *Bacteroidetes*.

The term "fingerprint" as used throughout the current disclosure refers to a set of experimental outcome with respect to the analysis of micro-organisms as will be obtained by applying the method according to the invention. Typically such "fingerprint" comprises information with respect to the population of micro-organisms, like phyla, relative amounts of micro-organisms and can for example be graphically represented in densiometric curves as shown in FIGS. 1 and 2. Such fingerprint thus describes a population of micro-organisms and in itself is not for describing individual bacteria within such population, although clearly such information can be obtained, for example by comparing to reference samples comprising a particular individual bacterial species.

In a preferred embodiment, the first and/or second taxonomic group is a phylum.

It has been found that the method according to the invention can be applied with advantage when the first and/or second taxonomic group is a phylum. It has been found that when a primer set P1 or P2 is directed to a conserved location L1 or L2, respectively, and that is specific for a phylum, it is now possible to not only detect fragments having detectable differences in size, number and/or nucleotide sequence, but by applying a suitable detection method (see below) also discriminate between different phyla.

By performing such method the sensitivity of the analysis of the population of micro-organisms, for example a bacterial population, is greatly enhanced. For example, it is now possible to discriminate between amplification fragments not only with respect to differences in size, and number, but also to assign a particular fragment to a specific phylum. In order words, where without using said primers which are specific for different phyla, only analysis was possible on the level of for example differences in size of obtained amplification fragments, now, and in the same method, one can discriminate also between different phyla in the same sample. This provides additional and essential information with respect to the (composition of a) population of micro-organisms, like a bacterial population, present in an environment, and thus with respect to the "fingerprint" of said population. In addition, one can now directly assign unknown microorganisms, like unknown bacterial species, to particular taxonomic groups, for example to which phylum an unknown species belongs.

In another preferred embodiment of the method, the primer sets P3 en P4 are identical.

With the term "identical" is, within the context of the current invention, intended that the primer set P3 that is directed to at least one conserved location L3 that is specific for the first taxonomic group, consists of at least one primer, wherein said primer of the primer set P3 is at the same time specific for the second taxonomic group, in order words, can be used as a primer for both taxonomic groups to be detected.

It has been found that when said primer set P3 and P4 are identical, a further improvement in the method for analysis ("fingerprinting") of a population of micro-organisms, like bacterial populations, can be achieved in comparison to when said primer sets P3 and P4 are not identical.

Without being limited or bound by any theory it is believed that when said primer sets P3 and P4 are identical, there appears to be less non-specific or false amplification of fragments in the sample. As a consequence more reliable and reproducible analysis of the population is achieved.

In addition it has been found that the information obtained with the method has improved reliability when it concerns the amount of a micro-organisms present in the population when primer sets P3 and P4 are identical. It is believed this is mainly due to the fact that possible differences in the efficiency of binding of the primer sets P3 and P4 to the conserved location are abolished when said sets are identical.

In another preferred embodiment there is provided a method for detecting alterations in a population of micro-organisms, like (for example) a bacterial population, present in an environment, comprising the steps of a. performing the method according to the invention on DNA obtained from said environment at a first time point t0; and b. performing the method according to the invention on DNA obtained from said environment at a second time point t1; and c. comparing the results obtained under step a and b.

As will be explained throughout the description, by performing said method it is now possible to detect alterations in a population of micro-organisms (e.g. bacterial population) present in an environment. In particular it is now for example possible to efficiently and reliably monitor changes in for example the alterations that occur in the gastro-intestinal tract in infants, for example as a consequence of the diet (e.g. breast milk versus artificial infant nutrition and milk formula's) or the treatment with drugs.

Also it is now possible to monitor for example recuperation of the population of micro-organisms after treatment with for example antibiotics.

As shown in the examples it is now even possible to detect variations in the composition of a population of micro-organisms on different places on or in the same organ (e.g. colon or skin or oral cavity), whereas at the same time classical methods like culturing bacteria sampled from such tissues fail (due for example to the fact that the micro-organisms are not viable after collection of the sample).

By comparing the amplification fragments obtained from an environment at a first time point with results obtained from an environment at a later time point, it can be determined whether in between these two time points, and for example as the consequence of an external factor like a drug, alterations in the population has occurred.

Likewise, by applying said method it can for example be monitored in time whether a population of micro-organisms (e.g. A bacterial population) is stable, fluctuates, or is developing in a particular direction, for example towards an already known healthy or beneficial (composition of the) a population of micro-organisms (e.g. bacterial population). In other words, comparison of the obtained results can also be to a particular "fingerprint" of a population of micro-organisms that, for example, is related to a known condition like disease or pollution.

In particular it has been found that the comparison can be made on the level of phyla, class, order, family, genus or species, preferably on the level of phyla.

Within the context of the current invention the term "on the level of" means that the comparison between the obtained results is made by comparing the information that has been obtained with respect to the taxonomic groups mentioned, for example, by comparison of the different phyla at time point t0 and t1 with respect to the number, amount and differences in size of the different fragments for a particular taxonomic group.

With the method according to the invention said comparison is now possible by comparing the "fingerprints" obtained at the different time points.

By comparison within a particular taxonomic group, preferably a phylum, and without the need to know in detail the individual microorganisms (e.g. bacterial species) present in a population, it can now advantageously and on a routine base be determined whether for example alterations in the population have occurred, without the need to know in detail what specific microorganisms (e.g. bacteria) has increased or changed.

Information on the level of for example a phylum can now be easily utilized to analyze whether for example beneficial alterations are occurring in time by comparing said information with known (compositions of) populations of micro-organisms (e.g. bacterial populations) related to such beneficial conditions.

For example, it can now be easily monitored whether, after treatment with a drug like antibiotics, the (compositions of a) population of micro-organisms (e.g. bacterial population) is recovering and developing towards a healthy or beneficial population.

According to a preferred method of the invention, the primer set P1 consists of one primer and/or the primer set P2 consists of one primer.

As has been described above, the primer set P1 and/or primer set P2 can comprise more than one primer directed to at least one conserved location (but also can comprise more than one primer or comprise primers directed to distinct conserved locations) that is specific for a particular first taxonomic group. Although advantageous results are obtained when said primer set comprising more than one primer, it has been found that in particular beneficial results are obtained when the primer set P1 and/or the primer set consists of one primer.

It will be understood by the person skilled in the art that obviously the primer set P1 and primer set P2 are not identical (in contrast to what can be the case for the primer sets P3 and P4).

It has been found that when the primer set P1 consists of one primer, the method according to the invention is improved with respect to the results obtained in comparison to when the primer set P1 comprises more than one primer. As has been explained above, it is believed this is due to diminishing possible differences in binding efficiency of the different primers present in a primer set to the conserved locations L1 in the different DNA's present in the sample, possibly introducing uncertainty in for example results with respect to the amount/concentration of a particular amplified fragment present is the sample. Said uncertainty is reduced when the primer set consists of one primer.

In another preferred embodiment of the method the method is characterized in that the primer set P3 and/or P4 consists of at least two, preferably at least three different primers.

It has been found that when the primer set comprises at least two, preferably at least three primers that are directed to at least one conserved location, analysis of the composition of a population of micro-organisms (e.g. bacterial population) is improved.

It has been found that be applying such primer set, the primer set can bind to different conserved locations in more different microorganisms (like bacteria) present in the sample (see above with respect to "conserved locations") in comparison to when the primer set consists of one primer.

As explained above, the term "directed to a conserved location" means that the primers comprised in a particular primer set can be efficiently used to detect at least 60%, preferably at least 70%, even more preferably 80%, even more preferably 90% of the different microorganisms (e.g. bacteria) known to belong to a particular taxonomic group, for example a phylum. In other words, at least the mentioned percentage of types of micro-organisms known to belong to a certain taxonomic group can be detected.

It has now be found that by combining at least two, preferably at least three different primers as described above, the percentage of detectable micro-organisms belonging to a taxonomic group can be increased.

For example, it can be found that a first primer p3 can be applied to detect up to 75% of the different types of bacteria belonging to a particular taxonomic group, but can not be applied to detect at least part of the undetected 25% of the bacteria due to, for example, the fact that the primer will not efficiently bind to the conserved location present in said bacteria due to mismatch in the nucleotide sequence of the primer.

By combining said first primer p3 with a second primer p3 and preferably with a third primer p3, the primer set P3 can now detect at least 90% of the types of different bacteria (microorganisms) belonging to a specific taxonomic group in a population.

For this, the sequences of the different primers comprised in the primer set will differ with respect to at least one nucleotide (A, T, C or G) from one and another. By having such primers in the primer set, the primer set can now also efficiently bind to microorganisms that comprise a conserved location at least specific for the particular taxonomic group, but differ in for example one, two, three of more nucleotides in comparison to another microorganism belonging to the same taxonomic group.

The results thus obtained are more representative and reliable in comparison to when the primer set P3 consists of one primer.

It can be envisaged that under circumstances clear for the person skilled in the art this may also comply with primer set P1 and P2, i.e. under conditions a primer set P1 and P2 comprising at least two primers might likewise be applied.

Further, it is clear from the description that in a more preferred embodiment, the primer set P3 and P4 are identical, but comprise of at least two, preferably at least three different primers.

Although the current invention is as such not limited to populations of micro-organisms (e.g. bacterial populations) from a particular environment, the method according to the invention is preferably performed on DNA derived from an environment selected from the group consisting of environments present in human, plant, animal, water, food (like dairy products), yeast cultures (e.g. used in industry), or soil, more preferably from an environment from gastrointestinal tract, skin, lung, sputum, colon, mouth, teeth pockets, ascetic fluid, faeces, purulence, abscess, wound fluid, wound, blood, or a cardiovascular system.

The person skilled in the art understands what these environments encompass, and this does not need any further elucidation in itself.

It has been found that now by performing the method according to the invention on DNA derived from said environments it is possible to provide useful, reliable and reproducible data of (the composition of) the population of micro-organisms (e.g. bacterial population) that is present in said environments, without the need to analyze the different species that might be present in such sample if far-reaching detail. However, as will be clear to the skilled person, such analysis can also suitably and preferably be performed by using the method according to the invention.

For example, the "fingerprint" thus obtained can be efficiently used to study differences between, alterations in or development of the population of micro-organisms (e.g. bacterial population) either by comparing to previously obtained results (fingerprint) that have been related to a particular condition (for example disease of pollution), or by following changes in time.

Alternatively, by once determining the presence of for example a pathogenic bacteria in an environment (by further applying methods known in the art directed to identifying individual bacteria), one can compare such data with a newly obtained fingerprint in order to establish whether such pathogenic bacteria might be present, without at least initially, the need, to proof the presence of said bacteria with the methods currently known in the art.

In another preferred embodiment, the said first and second primer sets P1 and P2 are labeled and comprise a label selected from the group consisting of a fluorescent label, preferably FAM™ (carboxyfluorescein), TET™ (tetrachlorofluorescein), HEX™ (hexachlorofluorescein), Cy5® (1-(ε-carboxypentyl)-1'-ethyl-3,3,3',3'-tetramethyl-5,5'-disulphonato-dicarbocyanine), Cy5.5® (1-(ε-carboxypentyl)-1'-ethyl-3,3,3',3'-tetramethyl-4,5,4',5'-(1,3-disulphonato)-dibenzo-dicarbocyanine), Cy3® (3-(ε-carboxypentyl)-1'-ethyl-3,3,3',3'-tetramethyl-5,5'-disulphonato-carbocyanine), Cy3.5® (3-(ε-carboxypentyl)-1'-ethyl-3,3,3',3'-tetramethyl-4,5,4',5'-(1,3-disulphonato)dibenzo-carbocyanine), Cy7® (1-(ε-carboxypentyl)-1'-ethyl-3,3,3',3'-tetramethyl-5,5'-disulphonato-tricarbocyanine), TAMRA™ (carboxytetramethylrhodamine), ROX™ (carboxy-X-rhodamine), JOE™ (6-carboxy-4',5'-dichloro-2',7'-dimethoxyfluorescein), FITC, TRITC, or radioactive label, preferably 3H, 14C, 32P or 33P, 35S.

After performing the amplification reaction according to the invention, fragments having detectable differences in size, number, and/or nucleotide sequence are obtained. Said differences can be detected by different methods known to the person skilled in the art.

For example, differences in nucleotide sequence can be determined by sequencing of the individual obtained fragments. Alternatively, the fragments can be analyzed by treating with endonucleases, thereby providing for example specific patterns comprised of parts of the obtained fragments. These patterns can than be compared to known patterns in order to further analyze the fragments. Alternatively, probes consisting of a particular sequence specific for example a certain taxonomic group, for example a phylum, can be used. For example, after obtaining the different fragments, a radioactive or fluorescent probe can be added to the sample and that specifically binds one of the taxonomic groups. A fingerprint of this particular taxonomic group can than be obtained by analyzing not only to which fragment the probe has hybridized (bound; attached), but also the different sizes of the thus labeled fragments. Likewise said detection can be performed for any other taxonomic group present in the sample and amplified by use of the different primers. Other methods of detection include mass-spectroscopy.

However, these methods might introduce uncertainty with respect to the reproducibility and reliability of the analysis. In contrast, it has been found that when the primers comprised in the primer set P1 and/or primer set P2 are labeled (and in case both primer set are labeled, obviously the primer sets are labeled with labels than can be discriminated from each other; see examples), for example with a radioactive label or both with a fluorescent label, the above problems do not appear to occur.

The amplified DNA can be labeled by using for example these fluorophore-labeled primers, requiring only unlabeled nucleotides for standard enzymatic incorporation. Labeling with labeled primers ensures efficient and unbiased incorporation of nucleotides, as the bulky dye molecule does not interfere with nucleotide incorporation, whereas in addition detection afterwards is greatly improved, most likely due to the fact that less steps are required in the detection, as the labeled obtained DNA fragments can be easily analyzed for example using an ABI PRISM® 3130xl Genetic Analyzer of Applied Biosystems, GENESCAN® Analysis software (Applied Biosystems) and the software package BIONUMERICS® 4.61 (Applied Maths), although alternative methods are known and available to the skilled person.

The labels described above are known to the person skilled in the art and can for example be obtained from Invitrogen (Carlsbad, Calif.). As will be understood by a person skilled in the art, preferably both the primer set P1 and the primer set P2 is labeled, with a different label, allowing to easily discriminate between the amplified fragments.

Therefore, according to another preferred embodiment of the method according to the invention, the label of primer set P1 is different from the label of primer set P2. For example the label of primer set P1 is fluorescent, and the label of primer set P2 is radioactive. More preferably both labels are fluorescent but can be discriminated from one and another.

As explained above, the method according to the invention is not limited to a primer set P1 and a primer set P2 that are specific for a taxonomic group, for example a phylum, but additional primer sets P can be introduced in the method.

For example, a first primer set P1 directed to a first phylum, a second primer set P2 directed to a second phylum, an additional primer set P-additional 1 directed to another phylum, and of course suitable primer sets P3 and P4 and additional primer set P-additional 2 in order to allow for amplification of a region between the conserved location L1-L3, L2-L4 and the region between the conserved L-additional locations op P-additional 1 and P-additional 2.

In a further embodiment of the method according to the invention, and when the first or second taxonomic group is a phylum, the phylum is selected from the group of phyla consisting of Firmicutes, *fusobacterium*, deferribacteres, spirochaetes, cyanobacteria, acidobacteria, nitrospina, nitrospirae, *caldithrix*, haloanaerobiales, verrucomicrobia, chlamydiae, planctomycetes, gemmimonas, fibrobacteres, chlorobi, bacteroidetes, proteobacteria, thermotogae, corprothermobacter, synergites, thermodesulfobacteria, *desulfurobacterium*, aquificae, deinococcus-thermus, chloroflexi and actinobacteria. In particular, firmicutes, bacteroidetes, *proteobacteria* and *actinobacteria* are preferred phyla.

These phyla are known to the person skilled in the art and have been described for example by Schloss in Microbiology and Molecular Biology Reviews, December 2004, volume 68(4):686-91), or in the renowned Bergey Manual, Second Edition 2004, Release 5.0.

For example, the phylum Bacteroidetes is composed of three large classes of bacteria that are widely distributed in the environment, including in soil, in sediments, sea water and in the guts of animals. By far, the Bacteroidales class are the most well-studied, including the genus *Bacteroides* (an abundant organism in the feces of warm-blooded animals including humans; including for example *B. acidifaciens, B. distasonis, B. gracilis, B. fragilis, B. oris, B. ovatus, B. putredinis, B. pyogenes, B. stercoris, B. suis, B. tectus, B. thetaiotaomicron, B. vulgatus*), and *Porphyromonas*, a group of organisms inhabiting the human oral cavity. Members of the genus *Bacteroides* are opportunistic pathogens. Rarely are members of the other two classes pathogenic to humans.

For example, while there are currently more than 274 genera within the Firmicutes phylum, notable genera of Firmicutes include: *Bacilli*, order Bacillales (*Bacillus, Listeria, Staphylococcus*); *Bacilli*, order Lactobacillales (*Enterococcus, Lactobacillus, Lactococcus, Leuconostoc, Pectinatus, Pediococcus, Streptococcus*); Clostridia (*Acetobacterium, Clostridium, Eubacterium, Heliobacterium, Heliospirillum, Sporomusa*); Mollicutes (*Mycoplasma, Spiroplasma, Ureaplasma, Erysipelothrix*).

It has been found that in particular the method according to the invention can be suitably utilized for analyzing (the composition of) a population of micro-organisms (e.g. bacterial population) in which said phyla are expected to be present. It has been found that in particular on the level of different phyla, the method provides experimental outcome/data that can advantageously be utilized in studying for example the effect of external factors on the development of population of micro-organisms (e.g. bacterial population), for example in the human gastro-intestinal tract. It is believed that analysis on the level of the phyla provides sufficient, reliable and useful data without the need to study in detail the multiple different species present in the sample.

With the method according to the invention it is thus now possible to obtain detailed information with respect to the composition of the population of micro-organisms (e.g. bacterial population) present in an environment by a simple procedure, not requiring detailed analysis on the level of a genus or species, thereby reducing the amount of experimental steps and primers required, strongly improving the reliability, reproducibility of both the quantitative and qualitative data obtained with respect to the population of micro-organisms (e.g. bacterial population). The method according to the invention does not only allow analysis of (the composition of) a population of micro-organisms (e.g. bacterial population), but in addition also allows for analysis of the relative presence of a (identified or unidentified) microorganism (like a bacteria) in the population.

Further there is disclosed a method according to the invention, characterized in that the pair of primer sets P1-P3 and/or the pair of primer sets P2-P4 is/are designed as described below.

In particular, there is provided a method according to the invention characterized in that the pair of primer sets P1-P3 and/or the pair of primer sets P2-P4 is/are designed by providing a) a first pair of primer sets P1-P3 that comprises at least a primer A and a primer B, wherein
  i) said primer A is a primer comprising at least 3-50, preferably 10-30 nucleotides, and wherein said primer is directed to a conserved location specific for a first taxonomic group;
  ii) said primer B is a primer comprising at least 3-50, preferably 10-30 nucleotides and wherein the region between the primer A and primer B is between 10-5000 nucleotides in microorganisms belonging to the first taxonomic group b) a second pair of primer sets P2-P4 that comprises at least a primer C and a primer D, wherein
  i) said primer C is a primer comprising at least 3-50, preferably 10-30 nucleotides, and wherein said primer is directed to a conserved location specific for a second taxonomic group;
  ii) said primer D is a primer comprising at least 3-50, preferably 10-30 nucleotides and wherein the region between the primer C and primer D is between 10-5000 nucleotides in microorganisms belonging to the second taxonomic group.

Obviously, the first and second taxonomic groups are different from each other.

It has been found that particularly advantageous results can be obtained with primer sets that are designed as described below.

Such primers are characterized in that they form two pair of primer sets P1-P3 and P2-P4 that are each specific for a taxonomic group, i.e. that can discriminate between different taxonomic groups. This can be achieved by having a primer set P1 and a primer set P2 that are each specific for different taxonomic groups, whereas the primer set P3 and P4 do not necessarily have to be specific for a specific taxonomic group (e.g. P3 might be identical to P4). In addition, the pair of primer sets can be determined by straight-forward comparison of sequences of known microorganisms that belong to a specific taxonomic group and comparison to a the primer set obtained for a second taxonomic group. The region between a particular pair of primer sets for use in the method according to the invention can for example be between 10 and 5000 nucleotides whereas the primers typically have a length of 3-50, preferably 10-30 nucleotides. By setting both the length of the primers and the length of the region between two primers in a pair of primer sets (e.g. P1-P3), by, for example computed, analysis of known sequences of micro-organisms, and if required subsequent analysis of regions (for example with respect to difference in length, size or sequence), a person skilled in the art can, with the disclosure here provided, determine suitable primers for use in primer sets for use in the method according to the invention.

Such primers, primer sets, pairs of primer sets and use thereof are thus explicitly meant to be encompassed by the current invention.

In general, suitable pair of primer sets can be designed as follows:

As described, in a primer-set P1, there is at least comprised a first primer p1 (primer A in this context of the invention) directed to a conserved location L1. This conserved location L1 is specific for a first taxonomic group, for example for a particular phylum. Therefore, in a first step for designing a suitable primer set, based on sequence information available from sequence databases, there is determined a location that is conserved in at least a substantial part of known species of the first phylum and to which a primer can be directed. For example, said sequence is determined in at least 3, 4, 5, preferably at least 10, or more known species that belong to the first taxonomic group.

As has been found in the current invention, it is preferred that the primer preferably is at least 3-50 nucleotides, more preferably 10-30 nucleotides in length. In order words, the conserved location (within the context of the current invention) that is to be determined is preferably also at least 3-50 nucleotides, more preferably 10-30 nucleotides in length.

For example in case of the nucleotide sequence shown below, a suitable primer can be determined:
Phylum X, 3 bacterial species X1, X2, X3

```
X1   acg tta act tcg gcc ggg aaa ggg ggg ttt   (SEQ ID NO: 8)

X2   tac acg gtg agc cat cat cat ggg ttt       (SEQ ID NO: 9)

X3   acg tca tca ctg ttc ccc ccc ggg ttt       (SEQ ID NO: 10)
```

An example of a suitable primer is such case would thus be a primer directed to the conserved location L1 acg as found in the sequences of X1, X2 and X3.

Likewise, a second primer (a primer B in this context of the invention; and thus a location L3) can be found by analysis of known sequences of the bacteria X1, X2 and X3. With respect to the current invention is has been found that preferably the region between L1 and L3 should be at least about 10 and at most about 5000 nucleotides. This person skilled in the art knows that for example, in the case of a length polymorphism, such region will have different lengths for different micro-organisms, for example for the different bacteria X1, X2 and X3. In other words, it has been found that for a second primer that is suitable in the primer set according to the invention, analysis of at most about 5000 nucleotides up- or downstream of the first primer suffices.

An example of a suitable second primer that together with the first primer might form a suitable primer set for use in the method according to the invention is shown below:
Phylum X, 3 bacterial species X1, X2, X3

```
X1   acg tta act tcg gcc ggg aaa ggg ggg ttt   (SEQ ID NO: 11)

X2   tac acg gtg agc cat cat cat ggg ttt       (SEQ ID NO: 12)

X3   acg tca tca ctg ttc ccc ccc ggg ttt       (SEQ ID NO: 13)
```

An example of a suitable primer is such case would thus be a primer directed to the conserved location L3 ttt as found in the sequences of X1, X2 and X3.

As can be witnessed from the example above, when using such primers for amplifying the region between the location L1 and L3, region with differences is size are obtained. In the current example the regions are 24, 18, and 21 nucleotides in length. As will be understood by the skilled person, said set of primers can be suitably used for detecting micro-organism of the same taxonomic group, as well as the different species within such taxonomic group.

In order to discriminate one taxonomic group from another however, in a next step it is determined whether a particular primer set directed to a conserved region is specific for a first phyla.

As described above, in any case, a location is conserved within the context of the current invention when it can be suitable used for binding of a primer allowing to discriminate micro-organisms from one taxonomic group from those of another, i.e. a primer is specific for at least one taxonomic group when it will not or essentially not bind to a substantial part of another taxonomic group that is to be analyzed in the method according to the invention (or when an amplification product cannot be obtained). For example a primer might detect phylum A and B, but not phylum C. In such case the primer is specific for phylum A en B, and is thus directed to a conserved location in phylum A and B, whereas said conserved location is absent in phylum C.

In order to establish whether the primer pair as designed above can suitably be used to discriminate a organisms of one taxonomic group from another, it must be determined that at least one of the conserved locations L1 or L3 is absent in, if not all, most of the known sequences of the second taxonomic group, or the region between the conserved regions L1 and L3 has a length unsuitable for performing an amplification reaction in the method according to the invention (e.g. more than 10,000 nucleotides).

For example, when determining a suitable primer set for a first phylum of bacteria X1, X2, X3 and X4 the following candidates where/could be identified (F-primer=forward primer; R-primer is reverse primer):

| F-primer | R-primer | Length X1 | X2 | X3 | X4 |
|---|---|---|---|---|---|
| ttgatcgat | agtcatat | 100 | 120 | 150 | 200 |
| gtacaagg | tacgcgga | 250 | 200 | 150 | 75 |
| acatcgac | atagatag | 200 | 150 | 250 | 300 |

As can be witnessed, the primer sets in the example can thus be suitably used for analysis of a species belonging to the said phylum. In the given examples, fragments will be obtained that differ in length and can thus be used to provide part of the fingerprint of the population of micro-organisms to be analyzed.

Likewise, when determining a suitable primer set (primers C and D within the context of this aspect of the invention) for a second phylum comprising bacteria Z1, Z2, Z3 and Z4 the following candidates where/could be identified (F-primer=forward primer; R-primer is reverse primer):

| F-primer | R-primer | Length Z1 | Z2 | Z3 | Z4 |
|---|---|---|---|---|---|
| gtagagag | cgtcgaaa | 200 | 150 | 120 | 300 |
| aagtcgctg | gtacgtcg | 80 | 70 | 180 | 100 |
| tgatcgatg | atagatag | 140 | 160 | 200 | 250 |

It can based on the primers thus be easily established that in the current example the reverse primer atagatag can be found in both phyla. In addition, the forward-primer Acatcgac from the first phylum is specific for said first phylum, and the forward primer tgatcgatg is specific for a second location. In other words, a pair of primer sets P1-P3 comprising the primers acatcgac and atagatag and a pair of primer sets P2-P4 comprising the primers tgatcgatg and atagatag, would, in the current example, be suitable primers for use in the method according to the invention as by use of such primers, the different phyla are discriminated from another, while in addition, fragments are obtained than can be easily discriminated based on differences in length (size). It has to be noted that in the current example the primer set P3 is identical to the primer set P4 (namely atagatag), although in other examples P3 and P4 might not turn out to be identical.

By means of the above disclosure, the person skilled in the art will understand how he can design primers suitable for use in the current invention, or determine whether particular primers are suitable primers in a primer set to be used in the method according to the invention.

Although, as explained above, the person skilled in the art can easily establish primers to be used in the method according to the invention, or determine whether a particular primer or set of primers can be applied with success in the method according to the invention, in particular good results have been obtained when the primer set P1 or P2 comprises a primer consisting essentially of DNA having a sequence selected from the group consisting of Seq ID No 1-2.

The first forward primer with Seq Id No. 1 is specific for the phyla Firmicuta and Actinobacteria and can for example be labeled with the fluorescent label FAM™ (carboxyfluorescein). The nucleotide sequence of said primer is:

```
FirISf:   5'-CTGGATCACCTCCTTTCTAWG-3'   (SEQ ID No 1)
```

The second primer with Seq Id No. 2 is specific for the phylum Bacteroidetes and can for example be labeled with the fluorescent label HEX™ (hexachlorofluorescein). The nucleotide sequence of said primer is:

```
BacISf:   5'-CTGGAACACCTCCTTTCTGGA-3'   (SEQ ID No 2)
```

As will be understood be the person skilled in the art, also encompassed are primers having essentially the sequence as described. In other words, primers wherein for example 1, 2, 3, or 4 nucleotides are altered in comparison to the sequences provided, or for example primers with a length that is 1, 2, 3, 4, or 5 nucleotides longer or shorter than the length of the primers provided above.

In another preferred embodiment the method is characterized in that the primer set P3 or the primer set P4 comprises a primer consisting essentially of DNA having a sequence selected from the group consisting of SEQ ID No 3, 4 and 5 (3-5).

These reverse primers can be non-labeled.

```
DUISr1:   5'-AGGCATCCACCGTGCGCCCT-3'   (SEQ ID No 3)
DUISr2:   5'-AGGCATTCACCRTGCGCCCT-3'   (SEQ ID No 4)
DUISr3:   5'-AGGCATCCRCCATGCGCCCT-3'   (SEQ ID No 5)
```

As will be understood be the person skilled in the art, also encompassed are primers having essentially the sequence as described. In other words, primers wherein for example 1, 2, 3, or 4 nucleotides are altered in comparison to the sequences provided, or for example primers with a length that is 1, 2, 3, 4, or 5 nucleotides longer or shorter than the length of the primers provided above.

As will be understood by a person skilled in the art, in particular a combination of more than one primers comprised in the primer set P3 or P4 can be applied with advantage, as discussed in detail above.

In particular it is preferred that when the primer set P1 comprises a primer consisting essentially of DNA having a sequence Seq ID No. 1 and when the primer set P2 comprises a primer consisting essentially of DNA having a sequence Seq ID No. 2, a primer set P3 or primer set P4 comprises a primer consisting essentially of DNA having a sequence selected from the group consisting of SEQ ID No. 3, 4 and 5.

By such combination good analysis of the composition of a population of micro-organisms (e.g. bacterial population) can be obtained, for example as shown in the examples.

AS a further example, a primer suitable for detecting the compositions of members belong to the Enterobacteriaceae can be given (Seq Id No 6) This primers was designed by using the method described above for finding suitable primers for use in the method according to the invention.

The forward primer with Seq Id No. 6 is can for example be labeled with the fluorescent label NED. The nucleotide sequence of said primer is:

```
Forward (DUISr4):
5' GGCATCCACCGTGTACGCT 3'      (SEQ ID No 6)
```

In another preferred embodiment the method is characterized in that for the primer described above (SEQ ID No 6) the primer set P3 or the primer set P4 further comprises a primer consisting essentially of DNA having a sequence of SEQ ID No 7.

```
Reverse (EntISf):
5' TTGGATCACCTCCTTACCTWA 3'    (SEQ ID No 7)
```

As will be understood be the person skilled in the art, also encompassed are primers having essentially the sequence as described. In other words, primers wherein for example 1, 2, 3, or 4 nucleotides are altered in comparison to the sequences provided, or for example primers with a length that is 1, 2, 3, 4, or 5 nucleotides longer or shorter than the length of the primers provided above.

In another preferred embodiment of the method according to the invention, the conserved location L1, L2, L3 or L4 is selected from the group consisting of a conserved region in the 16S rDNA region, the 23S rDNA region, the 5S rDNA region, the 16S-23S interspace region and the 5S-23S interspace region.

Said areas are known to the person skilled in the art and have been found to be in particular suitable locations for establishing primers suitably used as primers in for example primer set P1, primer set P2, or in primer set P3 and primer set P4.

The primers described in for example Seq Id No. 1-5 are examples of such suitable primers.

As explained above, the fragments obtained with the method according to the invention can be analyzed using several methods known in the art (sequencing, mass spectroscopy and the like).

Preferably, the obtained fragments comprise differences is size, and such differences are detected. In other words, the primers used in the different primer sets according to the invention are chosen as such that there is a difference is size with respect to the obtained fragments for the different types of microorganisms belonging to a specific taxonomic group.

Therefore a preferred method according to the invention is a method wherein the obtained fragments at least comprise differences in size.

In another aspect of the invention there is provided a primer or primer set suitable for use in the method according to the invention.

As explained above, the person skilled in the art, knowing the disclosure herein is without any inventive skill capable of determining whether a particular primer, a group of primers, or a primer set, either in combination with another primer set, is suitable for use in the method according to the invention.

For example, the primers described in Seq ID No 1-7 can be suitable used in the method according to the invention.

Therefore in another preferred embodiment, at least one primer is used in the current invention that consists essentially of DNA having a sequence selected from the group consisting of SEQ ID No 1-7.

According to another aspect of the current invention there is provided a combination of primer sets suitable for use as a pair of primer sets P1-P3 or P2-P4 in the method according to the invention.

As will be understood by the person skilled in the art, and as described herein, the method according to the invention is based on the amplification of at least a region between two conserved location L1 and L3 and/or L2 and L4. In other words, there must be provided a combination of primer sets suitable for use as a pair of primer sets P1-P3 or P2-P4 (and wherein P4 might be identical to P3).

In particular there is provided a combination of primer sets as described above, characterized in that at least one of the primers consists essentially of DNA having a sequence selected from the group consisting of SEQ ID No 1-7.

In another aspect there is provided a kit comprising at least a pair of primer sets P1-P3 and/or a pair of primer sets P2-P4 suitable for use in the method according to the invention.

Such kit might further comprise other components suitably used in the method according to the invention, like labeled primers, buffers, nucleotides, polymerase, incubation tubes, and the like, or instructions on how to perform a method according to the invention.

In another aspect there is provided the use of the method according to the invention, primers or primer sets suitable for use in the method according to the invention, for studying the effect of external factors on the composition of a population of micro-organisms (e.g. bacterial population) in an environment, wherein the external factor is selected from the group consisting of diet, food, drugs, antibiotics, temperature, probiotics, pollutants, pesticides, or medical treatment.

As explained herein the method according to the invention can suitably be used to, in a reliable manner, study the composition of a population of micro-organisms (e.g. A bacterial population). The thus obtained fingerprint of the population of micro-organisms (e.g. bacterial population) can for example also by compared with fingerprints from other, but comparable, environments (for example comparison between populations of micro-organisms (e.g. bacterial populations) from healthy subjects and subject suffering from a particular condition), or by comparison of the composition of the population of micro-organisms (e.g. bacterial population) obtained from the same environment but at different time points (for example, this allows to easily study the development of the composition of a bacterial population after for example antibiotic treatment, or after soil has been treated with pesticides or the like).

In this way, the effect of external factors that might influence the composition of a population of micro-organisms (e.g. bacterial population) can advantageously be analyzed with the method according to the invention.

In particular an external factor selected from the group consisting of diet, food, drugs, antibiotics, temperature, probiotics, pollutants, pesticides, or medical treatment can be easily monitored with respect to development or alteration in the composition of a population of micro-organisms (e.g. bacterial population).

As can be seen in the Examples provided, when performing a particular embodiment of the method according to the invention, there is provided information with respect to for example not only differences in size of the amplified fragments, but also to which particular taxonomic group, for example to which phylum, said fragment belongs. By means of the method, a general overview of the population of micro-organisms (e.g. bacterial population) present in an environment can thus be obtained, without the need of determining to which specific microorganism said obtained fragment belongs.

It will however be understood by the person skilled in the art that by simple comparison of the obtained results to the results obtained by applying the method according to the invention to DNA obtained from one specific microorganism (e.g. bacteria), further detailed analysis of the population of micro-organisms (e.g. bacterial population) can be performed.

In addition, it will be understood by the person skilled in the art that by comparing for example obtained results between samples obtained from different subjects, for example from healthy individuals and from individuals suffering from a particular condition, it can now easily be analyzed whether a particular condition is accompanied by a characteristic (composition of the) population of micro-organisms (e.g. bacterial population; fingerprint). For example it might be detected that in a condition X there is a change for example in the ratio between bacteria belonging to different taxonomic groups, for example phyla, while in addition it might be found that particular (unknown) bacteria belonging to a specific phylum are largely increased in the population, whereas others are absent in comparison to the population present in an healthy subject. In other words, the fingerprint of the population changed.

Likewise, the method according to the invention can advantageously be used for analyzing effects of external factors like diet, drugs, pesticides and the like on the composition of the population of micro-organisms (e.g. bacterial population).

Likewise, when comparing obtained information with respect to the composition of a population of micro-organisms (e.g. bacterial population) with compositions that are or have been related to specific conditions like a health condition, a diet or the presence of pesticides and the like in the environment, it can now for the first time be predicted whether such specific condition might also be present/occurring in the analyzed population of micro-organisms (e.g. bacterial population).

For example, when the consumption of particular fibers like galactooligosaccharides or fructooligosaccharides influences the composition of the population of micro-organisms (e.g. bacterial population) in a particular part of the gastro-intestinal tract in comprising more bacteria belonging to for example the phylum bacteriodetes, such specific fingerprint of the composition of the population of micro-organisms (e.g. bacterial population) can be compared to a fingerprint obtained from an individual in order to establish whether such person would for example be consuming food factors likewise influencing the composition of the population of micro-organisms (e.g. bacterial population) in said part of the gastro-intestinal tract.

It is thus with the method according to the invention now possible to better understand the relationship between (the composition of) a population of micro-organisms (e.g. bacterial population) and the influence of external factors thereon. The method can thus advantageously be used for studying, analyzing, predicting the role of external factors and/or conditions on the population of micro-organisms (e.g. bacterial population), and visa versa, without needing to known with particular microorganisms are present in the sample. The fingerprint of the population of micro-organisms (e.g. bacterial population) obtained by the method according to the invention can advantageously be used for said goals.

The invention will no be further exemplified by means of the non-limiting examples below. Although it will be understood be the person skilled in the art that the examples below do not limit the current invention, it is also to be understood that the mentioned methods, materials, conditions like temperature and concentration, primers and labels used, can, independently of the context within the examples, and within the current invention be regarded as to hold a preferred embodiment within the context of the current invention. For example when is mentioned that a reaction can be performed at 37-40° C. at a concentration of 2-50 mM, both 37-40° C. and 2-50 mM are, independently from each other, to be considered as favorable conditions and embodiments within the context of the invention.

EXAMPLES

Example 1

Samples

Human Gastro-Intestinal Tract:
Biopsy samples from human intestines were obtained during colonoscopy (samples can likewise be obtained my bioscopy of other parts of the intestines, including the small intestine.) The obtained samples weighed less than 25 mg and we immediately washed with 0.9% NaCl, frozen in liquid nitrogen and stored at −80° C. until use.

Example 2

DNA Isolation

In order to isolate DNA from the obtained samples, the obtained samples are first lysed. For this the QIAGEN QIAamp DNA Mini Kit is used, however the person skilled in the art will understand that other lysis protocols are available.

After thawing of the sample obtained under example 1, the sample is transferred to a tube comprising 360 µl ATL buffer. About 40 µl proteinase K is added. The resulting mixture is incubated at 56° C. until the tissue in the sample has lysed (about 1-2 hours). After spinning at 14,000 rpm for 5 seconds, 400 µl AL buffer is added. The mixture is thoroughly vortexed for 15 seconds and incubated, under shaking, for 10 minutes at 70° C.

Next, DNA isolation is continued by use of the easyMAG Biomérieux). For this, about 800 µl of the mixture is used, using the internal standard protocol with internal lysisstep. After performing the protocol as is present in the easyMAG, in total about 110 µl DNA in buffer is obtained.

Example 3

Primers

About 10-100 microliter of DNA as obtained in step 2 was used for the analysis according to the invention.

For this a PCR reaction was performed, although a person skilled in the art will understand that other means of amplification of DNA might be utilized.

The primers (0.1-1 microM, or more) used in the amplification in this example according to the invention are characterized in that the forwards primers are a such that they are specific for only a limited amount of phyla, for example for only one or only two different phyla. In addition, the primers are labeled with a different fluorescent label. The ratio DNA:primer can be varied between 1:1 to 1:50.

The first forward primer in the current example is specific for the phyla Firmicuta and Actinobacteria and is labeled with the fluorescent label FAM™ (carboxyfluorescein). The nucleotide sequence of said primer is:

```
FirISf:
5'-CTGGATCACCTCCTTTCTAWG-3'  (SEQ ID NO: 1)
```

The second primer is specific for the phylum Bacteroidetes en is labeled with the fluorescent label HEX™ (hexachlorofluorescein). The nucleotide sequence of said primer is:

```
BacISf:
5'-CTGGAACACCTCCTTTCTGGA-3'  (SEQ ID NO: 2)
```

Further, 3 non-labeled reverse primers were added to the mixture
These were:

```
DUISr1:   5'-AGGCATCCACCGTGCGCCCT-3' (SEQ ID NO: 3)

DUISr2:   5'-AGGCATTCACCRTGCGCCCT-3' (SEQ ID NO: 4)

DUISr3:   5'-AGGCATCCRCCATGCGCCCT-3' (SEQ ID NO: 5)
```

The PCR reaction was performed in a GeneAmp PCR System 9700 of Applied Biosystems. The following mixture was prepared for each independent PCR reaction:

|  | Stock | Per reaction (μl) |
|---|---|---|
| PCR Buffer Gold | 10x | 2.5 |
| DNTP | 2 mM | 2.5 |
| MgCl2 | 25 mM | 1.5 |
| BSA | 1.25% | 0.8 |
| Ampli TAQ Gold | 5 U/ul | 0.2 |
| Bidest | 100% | 4 |
| FirISf | 10 μM | 0.7 |
| BacISf | 10 μM | 0.7 |
| DUISr1 | 10 μM | 0.7 |
| DUISr2 | 10 μM | 0.7 |
| DUISr3 | 10 μM | 0.7 |

The PCR cycle was as follows:

7 min 94° C.
30 sec 94° C.
45 sec 56° C.   } 35x
1 min 72° C.
5 min 72° C.

Example 4

Fragment Analysis

After the PCR, the obtained fragments were analyzed using an ABI PRISM® 3130xl Genetic Analyzer of Applied Biosystems, GENESCAN® Analysis software (Applied Biosystems) and the software package BIONUMERICS® 4.61 (Applied Maths).

Example 5

Results of a Typical Performing of the Method According to the Invention

The results below in FIG. 1 were obtained from 5 biopsy samples obtained from human intestines as described above.

In FIG. 1, from left to right, the length of the fragments runs from 0 base pairs to 1000 base pairs. The small peaks indicated with an "s" are examples of size markers, allowing relating the size of the different obtained fragments.

Peaks indicated with a "B" represent HEX™ (hexachlorofluorescein)-labeled fragments of bacteria from the phylum Bacteroidetes.

Peaks indicated with a F are examples of FAM™ (carboxyfluorescein)-labeled products of bacteria from the phyla Firmicuta en Actinobacteria.

By relating the position on the x-axis with the size marker, the exact length of the fragments is determined. Such data can for example be related to specific information already acquired with respect to one or more specific bacterial genus of species. It is believed that the height of the peaks represent with de amount of the particular bacteria present in the population.

It is clear from the results that the different subjects display different fingerprints, and that within the fingerprint in some subjects peaks are present while these are absent in other, while at the same time similarities between the different subjects can be observed.

Example 6

In FIG. 2, the method according to the invention, as described above is applied to a so-called mixed culture of *Enterococcus faecalis* (belonging to the Firmicuta) and *Bacteroides fragilis*, belonging to the phylum Bacteroidetes. As can be seen from the figure, the method allows for discrimination between the two different bacteria, but more important said data can now be easily used by comparing the obtained "fingerprint" with fingerprints of population of micro-organisms (e.g. bacterial populations), allowing, without the need of specific primers for such bacteria, easy and straight-forward identification of such micro-organisms (e.g. bacteria) present in the population of micro-organisms (e.g. bacterial population).

Example 7

An experiment was performed to study the "fingerprint", i.e. the complex composition of the bacterial population sampled from different locations in the colon. In addition the feces were analyzed with the method according to the invention.

For this colonoscopy by methods known in the art was performed on 20 healthy subjects. This procedure was performed based on genetic predisposition for intestinal disease. For all the subjects used in this analysis, colonoscopy and histology performed on colonic biopsies showed no abnormalities. For each patient 5 biopsies were taken throughout the entire colon and rectum. Locations of biopsies were: caecum (CC), hepatic flexure (HC), splenic flexure (LC), sigmoid (SC) and rectum (RC).

Some days (e.g. 3 days) after colonoscopy, feces was collected. DNA isolation and profile generation from all samples was performed as described above, using the primers and primer pairs described in the current application. Cluster analysis of the results (using Pearson correlation and UPGMA) showed that for every subject, microbial profiles (as generated by the method according to the invention) were almost identical throughout the colon and rectum.

Figure 3:
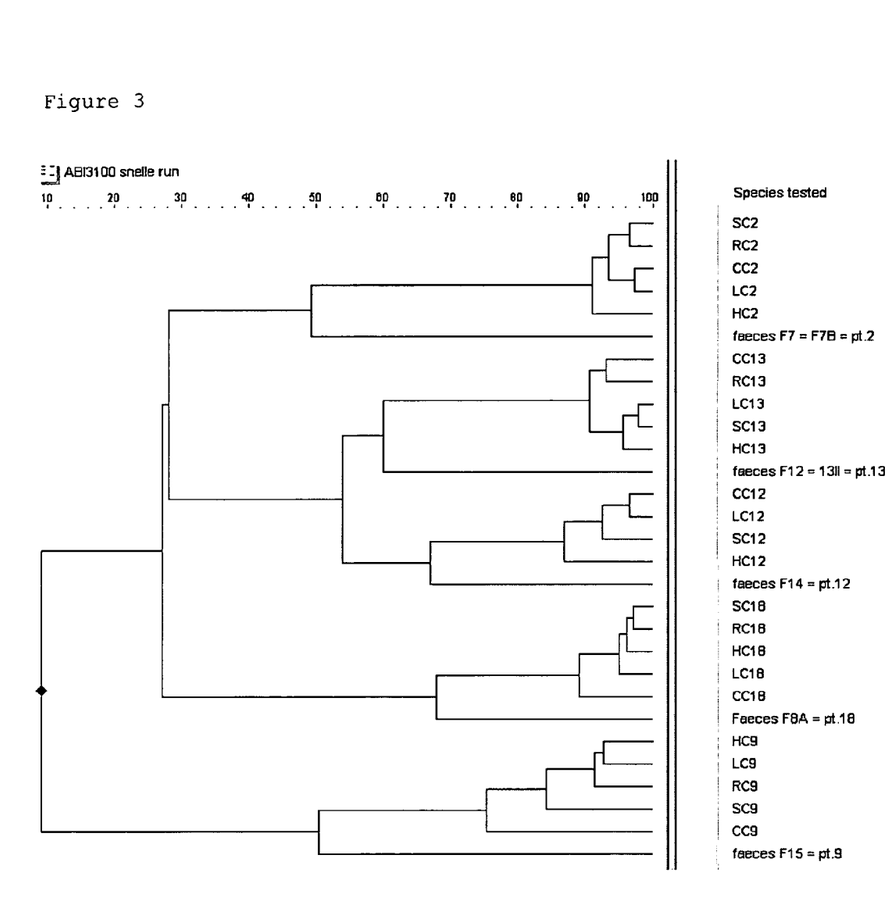
FIG. 3 shows cluster analysis of colonic biopsies and faeces of 5 subjects.

Interindividual variations of profiles was however very large: every patient had an own, unique profile. Profiles obtained from feces, showed significant differences from biopsies, but faecal profiles were still patient-specific: rather than cluster with other faecal samples, profiles still clustered with biopsy profiles of the same patient (FIG. 3; FIG. 3 shows cluster analysis of colonic biopsies and faeces of 5 subjects. While differing significantly, faecal profiles still cluster with colonic profiles from the same subject.).

This example clearly shows that the method according to the invention is excellent for analysis of colonic biopsies specimens regardless of anatomic site of the biopsy. Furthermore, faecal profiles are correlated to biopsy profiles of the same subject and are also extremely suitable as input for the method according to the invention (IS-Pro). This data also confirms the reproducibility of the method according to the invention.

Example 8

Further evaluation of the suitability of the method according to the invention for studying and determining fingerprints, i.e. the compositions of microorganisms present in a sample (without the need to indeed know the microorganisms in detail and beforehand) for example present in faeces was performed. The goal of the experiment was to establish whether variations in the compositions of the microbiome (for example induced by external factors like diet, medicine, alcohol) could be detected.

For this, 7 faecal samples from a healthy subject were obtained over a 2 week period. Analysis of profiles generated by the method according to the invention was performed by using the BioNumerics software package. This analysis revealed that Bacteroidetes present in faeces were stable over time, whereas Firmicutes showed variation throughout the period. This variation could be correlated to alcohol consumption of the subject the day before the sample was taken. This data emphasizes and proofs that the method according to the invention is a sensitive method, very suitable for detecting variations in composition of the microbiome (induced by external factors like alcohol, diet and or drugs).

Example 9

Gut Microbiome Development and Effect of Antibiotic Intervention

In a group of 5 newborn babies, faeces was collected at day 7, 14 and 30 after birth. One of the babies (child 5), had received antibiotics during a large fraction of the study period. Using the method according to the invention, profiles (fingerprints) were generated from all samples. Profiles were analyzed and cluster analysis was performed as described above.

Figure 4:
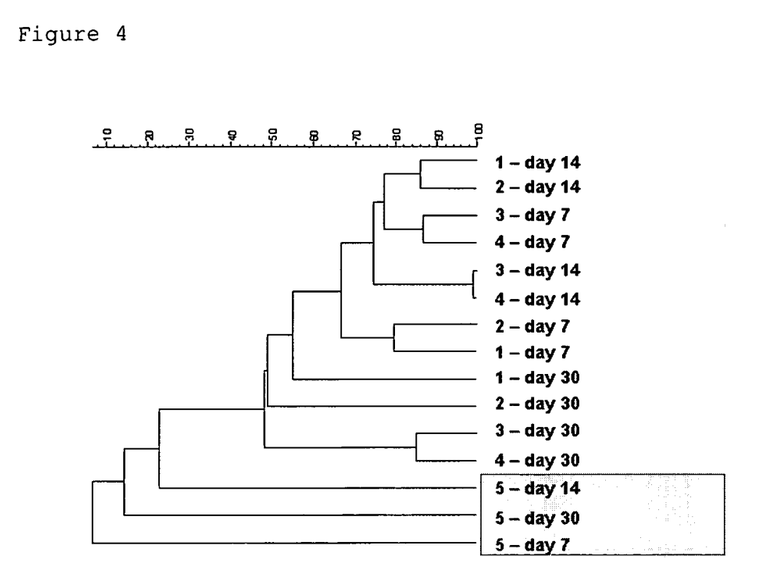
FIG. 4 provides a dendogram created by UPGMA showing strong correlation through time for all children except for child 5, the child that had received antibiotics.

Results showed that the profiles of children 1-4 showed correlation to each other through time, with child 1 and 2 and child 3 and 4 showing strong pair wise similarity. At day 30 profiles start to differentiate. Profiles from child 5—the child that had received antibiotics—showed no correlation to those obtained from the other children or to each other throughout the entire study period (FIG. 4; FIG. 4 dendogram created by UPGMA showing strong correlation through time for all children except for child 5, the child that had received antibiotics.).

This experiment shows that antibiotic intervention can have a great impact on intestinal microbiome composition and that such changes can be readily assessed by the method according to the invention.

Example 10

Skin Microbiome

To evaluate applicability of the method according to the invention for analysis of skin microbiome, retroauricular skin swabs were taken from 5 subjects. One of these five subjects had an infected skin lesion. From this lesion too, a swab was taken. From these skin swabs, DNA was isolated as described above and profiles were generated with the method according to the invention. Analysis of profiles showed that skin microbiome was very similar between subjects. The profile obtained from the infected skin lesion differed significantly from retroauricular swab of that subject and from all other subjects. From this we conclude that the method according to the invention is suitable for analysis of the complex microbiome found on the skin and that detection of variation of this profile as found for example in lesions of the skin, is very straightforward using this method.

Example 11

Oral Microbiome

To evaluate applicability of the method according to the invention for analysis of oral microbiome, mouth swabs were taken from 5 healthy subjects. One of these five subjects had an aphtoid ulceration of the oral mucosa. From this lesion too, a swab was taken. From these oral swabs, DNA was isolated as described above and profiles were generated. Analysis of profiles showed that oral microbiome was more variable between subjects than skin microbiome, but far less variable than intestinal microbiome. The profile obtained from the aphtoid lesion differed significantly from oral swab taken from non-ulcerated mucosa of that subject. From this we conclude that the method according to the invention is suitable for analysis of the oral microbiome and that detection of variation of this profile as found for example in aphtoid lesions, is very straightforward using this method.

The invention claimed is:

1. A method for analyzing a microbial population of an environment suspected to contain populations of micro-organisms comprising the steps of:
   a) providing DNA obtained from said environment and providing thereto at least
      i) a first primer set P1, comprising at least one primer p1, that is directed to at least one conserved location L1 specific for a first taxonomic group selected from the group consisting of phylum, class, order or family; and
      ii) a second primer set P2, comprising at least one primer p2, that is directed to at least one conserved location L2 specific for a second taxonomic group selected from the group consisting of phylum, class, order or family; and
      iii) a third primer set P3, comprising of at least one primer p3, that is directed to at least one conserved location L3 that is at least specific for micro-organisms belonging to the first taxonomic group; and
      iv) a fourth primer set P4, comprising of at least one primer p4, that is directed to at least one conserved location L4 that is at least specific for micro-organisms belonging to the second taxonomic group, and wherein the primer sets P1 and P3 are suitable for amplifying a region between said conserved regions L1 and L3 and wherein the primer sets P2 and P4 are suitable for amplifying the region between said conserved regions L2 and L4;
   wherein the region between conserved locations L1 and L3 that can be amplified by a primer pair from the combination of primer sets P1 and P3, differs with regard to sequence length between microorganisms belonging to the first taxonomic group, and wherein the region between conserved locations L2 and L4 that can be amplified by a primer pair from the combination of primer sets P2 and P4, differs with regard to sequence length between microorganisms belonging to the second taxonomic group,
   wherein the first and second primer set P1 and P2 are labeled, wherein the label for primer set P1 is different from the label of primer set P2;
   b) performing a single amplification reaction using said primer sets, thereby producing amplified products representative of the populations of microorganisms within said taxonomic groups with detectable differences in length, amount, and label, and
   c) detecting the said differences in length, amount, and label of the amplified products of step b).

2. The method of claim 1, wherein the population of micro-organisms comprises bacteria.

3. The method of claim 1, wherein the first and/or second taxonomic group is a phylum.

4. The method of claim 1, wherein said primer set P3 and said primer set P4 are identical.

5. A method for detecting alterations in a population of microorganisms present in an environment comprising the steps of:
   a) performing the method of claim 1 on DNA obtained from said environment at a first time point t0;
   b) performing the method of claim 1 on DNA obtained from said environment at a second time point t1; and
   c) comparing the results obtained under step a and b.

6. The method of claim 5, wherein the comparison is made on the level of phyla, class, order, family, genus or species.

7. The method of claim 1 or 5, wherein the primer set P1 consists of one primer and/or the primer set P2 consists of one primer.

8. The method of claim 1 or 5, wherein the primer sets P3 and/or P4 consists of at least two different primers.

9. The method of claim 1 or 5, wherein the DNA is derived from an environment selected from the group consisting of microbial environment present in human, plant, animal, water, food, or soil.

10. The method of claim 1 or 5, wherein said first and second primer sets P1 and P2 are labeled and comprise a label selected from the group consisting of a fluorescent label, FAM™ (carboxyfluorescein), TET™ (tetrachlorofluorescein), HEX™ (hexachlorofluorescein), Cy5® (1-(ϵ-carboxypentyl)-1'-ethyl-3,3,3',3'-tetramethyl-5,5'-disulphonato-dicarbocyanine), Cy5.5® (1-(ϵ-carboxypentyl)-1'-ethyl-3,3,3',3'-tetramethyl-4,5,4',5'-(1,3-disulphonato)-dibenzo-dicarbocyanine), Cy3® (3-(ϵ-carboxypentyl)-1'-ethyl-3,3,3',3'-tetramethyl-5,5'-disulphonato-carbocyanine), Cy3.5® (3-(ϵ-carboxypentyl)-1'-ethyl-3,3,3',3'-tetramethyl-4,5,4',5'-(1,3-disulphonato)dibenzo-carbocyanine), Cy7® (1-(ϵ-carboxypentyl)-1'-ethyl-3,3,3'',3'-tetramethyl-5,5'-disulphonato-tricarbocyanine), TAMRA™ (carboxytetramethylrhodamine), ROX™ (carboxy-X-rhodamine), JOE™ (6-carboxy-4',5'-dichloro-2',7'-dimethoxyfluorescein), FITC, TRITC, radioactive label, 3H, 14C, 32P, 33P, and 35S.

11. The method of claim 1 or 5, wherein when the first or second taxonomic group is a phylum, the phylum is selected from the group of phyla consisting of firmicutes, *fusobacterium*, deferribacteres, spirochaetes, cyanobacteria, acidobacteria, nitrospina, nitrospirae, *caldithrix*, haloanaerobiales, verrucomicrobia, chlamydiae, planctomycetes, gemmimonas, fibrobacteres, chlorobi, bacteroidetes, proteobacteria, thermotogae, corprothermobacter, synergites, thermodesulfobacteria, *desulfurobacterium*, aquificae, deinococcus-thermus, chloroflexi and actinobacteria.

12. The method of claim 1 or 5, wherein the pair of primer sets P1-P3 and/or the pair of primer sets P2-P4 is/are designed by providing:
   a) a first pair of primer sets P1-P3 that comprises at least a primer A and a primer B, wherein
      i) said primer A is a primer comprising at least 3-50 nucleotides, and wherein said primer is directed to a conserved location specific for a first taxonomic group;
      ii) said primer B is a primer comprising at least 3-50 nucleotides and wherein the region between the primer A and primer B is between 10-5000 nucleotides in microorganisms belonging to the first taxonomic group;
   b) a second pair of primer sets P2-P4 that comprises at least a primer C and a primer D, wherein
      i) said primer C is a primer comprising at least 3-50 nucleotides, and wherein said primer is directed to a conserved location specific for a second taxonomic group;
      ii) said primer D is a primer comprising at least 3-50 nucleotides and wherein the region between the primer C and primer D is between 10-5000 nucleotides in microorganisms belonging to the second taxonomic group.

13. The method of claim 1 or 5, wherein the primer set P1 or P2 comprises a primer consisting essentially of DNA having a sequence selected from the group consisting of SEQ ID NOS: 1-2.

14. The method of claim 1 or 5, wherein the primer set P3 or the primer set P4 comprises a primer consisting essentially of DNA having a sequence selected from the group consisting of SEQ ID NOS: 3-5.

15. The method of claim 1 or 5, wherein the primer set P1 or P2 comprises a primer consisting essentially of DNA having a sequence of SEQ ID NO: 6.

16. The method of claim 1 or 5, wherein the primer set P3 or the primer set P4 comprises a primer consisting essentially of DNA having a sequence of SEQ ID NO: 7.

17. The method of claim 1 or 5, wherein the conserved location L1, L2, L3 or L4 is selected from the group consisting of a conserved region in the 16S rDNA region, the 23S rDNA region, the 5S rDNA region, the 16S-23S interspace region and the 5S-23S interspace region.

18. A method for studying the effect of external factors on a population of micro-organisms in an environment comprising the steps of:
   a) performing the method of claim 1 on DNA obtained from an environment under a first set of external factors;
   b) performing the method of claim 1 on DNA obtained from an environment under a second set of external factors; and
   c) comparing the results obtained under step a and b,
wherein the external factor is selected from the group consisting of diet, food; drugs; antibiotics, temperature, probiotics, pollutants, pesticides, and medical treatment.

19. The method of claim 1 or 5, wherein the primer sets P3 and/or P4 consists of at least three different primers.

20. The method of claim 1 or 5, wherein the DNA is derived from an environment selected from the group consisting of a microbial environment from gastro-intestinal tract, skin, lung, sputum, colon, mouth, ascetic fluid, faeces, abscess, purulence, teeth pockets, wound fluid, wound blood, and cardiovascular system.

* * * * *